United States Patent
Kolberg

(10) Patent No.: US 8,428,750 B2
(45) Date of Patent: Apr. 23, 2013

(54) IMPLANTABLE MEDICAL ELECTRODE DEVICE

(75) Inventor: Gernot Kolberg, Berlin (DE)

(73) Assignee: Biotronik CRM Patent AG (CH)

( * ) Notice: Subject to any disclaimer, the term of this patent is extended or adjusted under 35 U.S.C. 154(b) by 1311 days.

(21) Appl. No.: 11/688,360

(22) Filed: Mar. 20, 2007

(65) Prior Publication Data

US 2007/0233218 A1 Oct. 4, 2007

(30) Foreign Application Priority Data

Mar. 30, 2006 (DE) .................. 10 2006 014 698

(51) Int. Cl.
*A61N 1/05* (2006.01)

(52) U.S. Cl.
USPC .................. 607/126; 600/375; 600/381

(58) Field of Classification Search .......... 607/122, 607/126, 128, 130; 600/373, 375, 381
See application file for complete search history.

(56) References Cited

U.S. PATENT DOCUMENTS

| 4,301,815 A | 11/1981 | Doring |
| 4,825,871 A | 5/1989 | Cansell |
| 6,181,973 B1 * | 1/2001 | Ceron et al. ......... 607/126 |
| 2004/0230282 A1 | 11/2004 | Cates et al. |

FOREIGN PATENT DOCUMENTS

| DE | 35 10821 A1 | 10/1985 |
| DE | 699 21 447 T2 | 11/2005 |

* cited by examiner

*Primary Examiner* — Carl H Layno
*Assistant Examiner* — Jessica Sarcione
(74) *Attorney, Agent, or Firm* — Craig A. Fieschko, Esq.; DeWitt Ross & Stevens S.C.

(57) ABSTRACT

A medical, implantable electrode device, in particular a cardiological electrode device, comprises an elongate electrode body (2) having a proximal and a distal end (1) for insertion into the body of the patient and multiple strut-like anchoring elements (4), which are attached laterally to the electrode body (2) before the distal end (1) for fixing the electrode device in the patient and are distributed around the circumference, which each project having their longitudinal axis (SL) at an acute angle (W1) opening in the direction of the proximal end in relation to the electrode body axis (KL). The anchoring elements have a preferred direction around the circumference in such a way that upon engagement of the anchoring elements (4) in a body part of the patient, a rotation of the electrode body (2) is opposed by a greater resistance in one rotational direction than in the opposite direction.

20 Claims, 2 Drawing Sheets

IMPLANTABLE MEDICAL ELECTRODE DEVICE

FIELD OF THE INVENTION

The present invention relates to a medical, implantable electrode device and particularly a cardiological electrode device such as a cardiac catheter.

BACKGROUND OF THE INVENTION

In the field of cardiac electrodes, it is typical to attach anchoring elements, which are used for fixing the electrode device in the body of the patient, laterally to the electrode, distributed around its circumference in the area of the distal end of the elongate electrode body, which is inserted into the patient body. These anchoring elements are wing-like struts made of soft plastic which are injection molded onto the electrode body, which hook in the trabeculae of the ventricle and are thus to ensure fixing of the electrode body. These anchoring elements, generally referred to as "tines", each have their longitudinal axis projecting from the electrode body axis at an angle opening in the direction of the proximal end of the electrode body, in order to counteract withdrawal of the electrode tip from its anchoring point.

Further applications of the present invention may also be electrodes implantable in vessels, such as a coronary sinus electrode, which is in turn fixed in a coronary sinus via anchoring elements along its electrode body—i.e., all having some proximal distance in front of the distal end.

In the known electrode devices, the problem may occur that the anchoring elements may snag on other body structures, for example, in the valve leaflets, during insertion or withdrawal of the catheter. This results in the electrode having to be freed using a relatively strong pull on the electrode body, which may result in local damage to the cardiac tissue. Possible solutions for these problems of the anchoring elements have been suggested in that they may be inserted and retracted by a mechanical controller. However, this has a very complex construction and is also susceptible to breakdown because of the very fine structures of the anchoring elements.

SUMMARY OF THE INVENTION

Proceeding therefrom, the present invention is based on the object of improving the known electrode devices in regard to their anchoring elements in such a way that implantation and explantation of the electrode device with less interference, but nonetheless reliable fixing, are ensured.

This object may be achieved by providing the anchoring elements with a preferred direction around the circumference in such a way that upon insertion of the anchoring elements into a body part of the patient, a rotation of the electrode body is opposed by a greater resistance in a predefined rotational direction than in the opposite direction.

This design results in the implanter setting the electrode body in rotation in the rotational direction in which he feels a lower rotational resistance, if the anchoring elements snag in the valve leaflets, for example. This rotation anisotropy may, for example, be achieved by a tilted configuration of anchoring elements in relation to a radial plane spanned by the electrode body axis and the base point of the particular anchoring element. The strut-like anchoring elements thus project diagonally from the electrode body in relation to the peripheral direction. This means that they stand up upon rotation in one direction in the event of an external resistance, such as the trabeculae in the heart, and thus tangle more strongly with the surrounding tissue. Upon a rotation in the opposite direction, the anchoring elements adapt to the electrode body, so that they disengage from the external tissue and the electrode body is thus simpler to withdraw from its fixing in the trabeculae or easier to detach from a snag in the valve leaflets, for example.

In preferred versions of the invention, the directional anisotropy of the anchoring elements may also be achieved by a curved implementation around the circumference in relation to the electrode body or by a corresponding anisotropic flexural strength of anchoring elements.

The present invention may also be applied in a vascular electrode, such as a coronary sinus electrode. In a corresponding refinement, the anchoring elements are formed by multiple lamellae, which are distributed around the circumference of the electrode body, project essentially radially, and extend in the longitudinal direction of the electrode body, and which have a curved course in relation to the radial direction.

The latter also implements a concept of the present invention, namely the anisotropic resistance in relation to the rotation of the electrode body. Thus, for example, spreading of the projecting lamellae may be achieved by a right rotation of the electrode body, which causes secure anchoring of the electrode in the vessel.

Further features, advantages, and details of the present invention may be inferred from the following description, in which exemplary embodiments are explained in greater detail on the basis of the attached drawing.

DETAILED DESCRIPTION OF PREFERRED VERSIONS OF THE INVENTION

Figure 1:
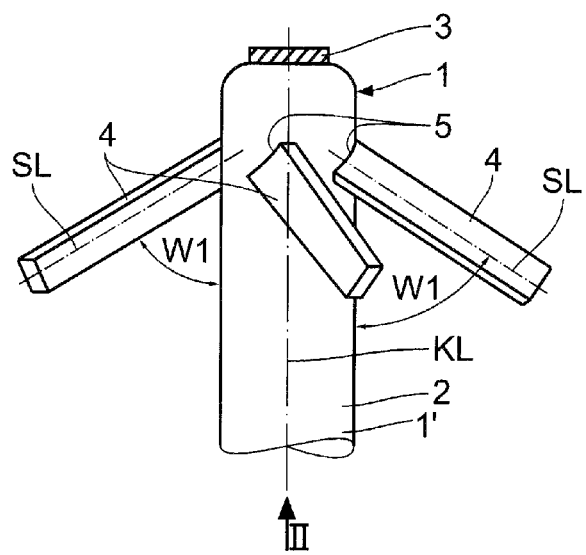
FIG. 1 shows a side view of the distal end of a cardiac catheter.
Figures 2, 3:
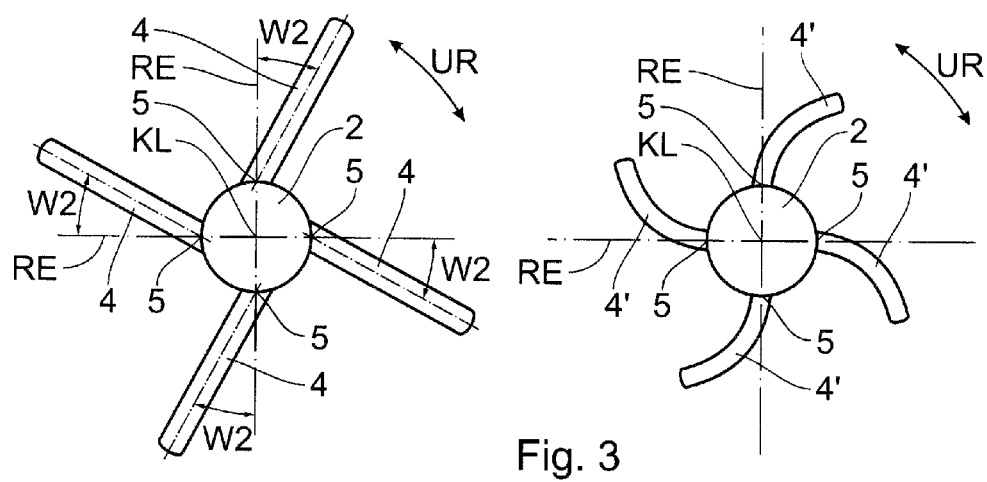
FIG. 2 shows a view of the distal end from arrow direction II in FIG. 1.
FIG. 3 shows a frontal view analogous to FIG. 2 of a cardiac catheter in an alternative embodiment.

The two illustrations in FIGS. 1 and 2 show the distal end of 1 of an electrode body 2 of a cardiac catheter which is to be anchored in the trabeculae in the ventricle of the heart, for example. A cardiological potential may be measured and/or a voltage pulse may be delivered via the tip electrode 3 shown in FIG. 1, for example, if the cardiac catheter is used with a cardiac pacemaker.

To anchor the distal end 1 having its tip electrode 3, laterally projecting anchoring struts distributed around the circumference, which are made of an elastic plastic material—such as silicone—are injection molded directly onto the electrode body 2 before the end. These anchoring struts 4 project with their longitudinal axis SL at an acute angle W1, of 60 degrees for example, opening in the direction of the proximal end (approximated at 1') to the body longitudinal axis KL of the electrode body 2. As may be seen in FIG. 1 and more clearly in FIG. 2, the four anchoring struts 4 are additionally tilted out at an acute angle W2 from the radial plane RE spanned by the body longitudinal axis KL and the base point 5 of anchor strut 4. The angle W2 is preferably approximately 30 degrees, the tilting direction of each anchoring strut 4 pointing clockwise in each case in relation to a view direction originating from the proximal end 1'. This has the result that upon a rotation of the electrode body 2 clockwise to anchor the distal end 1 in the trabeculae of the ventricle, for example, a reinforced anchoring effect results, as well as rotational resistance dependent on the direction of rotation. As the electrode body 2 is "screwed in", i.e., as it is rotated clockwise in relation to FIG. 2, the anchoring elements 4 stand up against the trabeculae, which results in an increase of the rotational resistance. The implanter thus intuitively feels that the distal end 1 anchors in the trabeculae.

To detach the electrode body 2—in case of interference of a snag of anchoring struts 4 in the valve leaflets, for example—the electrode body 2 is rotated counterclockwise, i.e., "unscrewed", with the anchoring struts 4 recognizably pressing against the electrode body 2 and the engagement of anchoring struts 4 in the trabeculae thus being noticeably reduced. A further advantage of the tilting of the anchoring struts 4 is that as they are "screwed in", the anchoring struts 4 may slide behind projections in the body or under undercut areas, which would not be reachable without the tilted position. The implanter may also form an impression of the state of the fixing of the electrode at the appropriate point on the heart by the resulting rotational resistance. He thus receives a "feeling" for the degree of fixing, without having to pull on the electrode.

An alternative for producing an anisotropic rotational resistance is illustrated in FIG. 3. The anchoring struts 4' begin at the electrode body 2 coplanar with the radial plane RE, but are designed as curved clockwise, through which a resistance increase also results here upon rotation clockwise in relation to FIG. 3, and weakening of the resistance results upon rotation counterclockwise. The anchoring struts 4' also preferably project at an acute angle W1 to the body longitudinal axis KL, analogously to the struts 4 in FIGS. 1 and 2.

While not shown in greater detail in the drawing, the rotational direction anisotropy may also be implemented by an anisotropic flexural strength of the anchoring struts 4 in relation to the peripheral direction UR.

Figure 4:
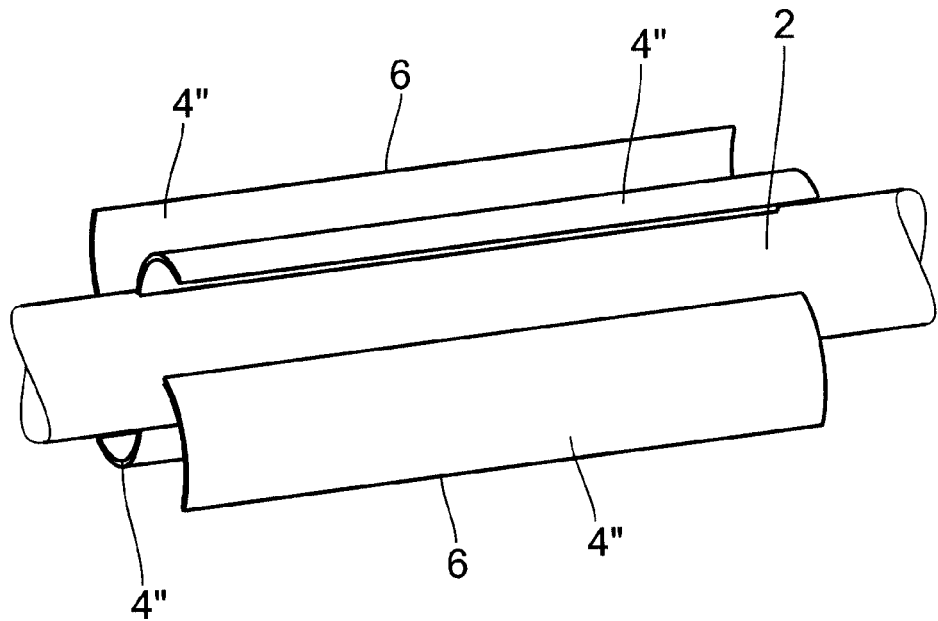
FIG. 4 shows a detail perspective view of an anchoring zone of a coronary sinus electrode.
Figure 5:
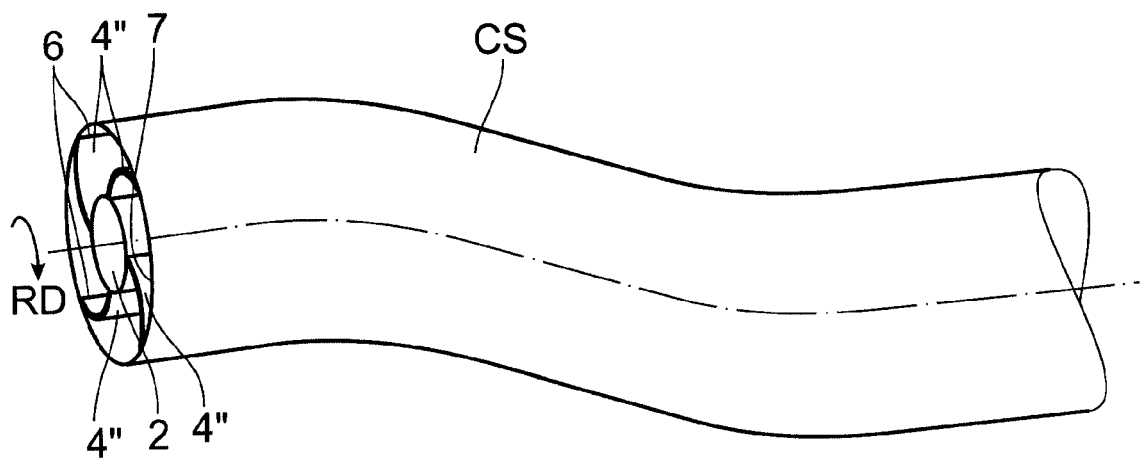
FIG. 5 shows a schematic illustration of the electrode from FIG. 4 in its position in the coronary sinus.

The embodiment of the electrode device shown in FIGS. 4 and 5 illustrates (in detail) a coronary sinus electrode, whose electrode body 2 is possibly provided with anchoring elements in the form of lamellae 4" at multiple positions proximally in front of its distal end (not shown here). Four of these lamellae 4" are distributed uniformly around the circumference of the electrode body 2 and their main direction extends in the longitudinal direction of the electrode body 2. The lamellae 4" have a curved shape in relation to the radial direction, as is clear from FIGS. 4 and 5.

The purpose of the curved shape is clear from FIG. 5. The lamellae 4" spread out against the vascular wall 7 in the event of a right rotation RD of the electrode body 2 due to the leading front edge 6 of the lamellae 4", through which good anchoring of the electrode in the coronary sinus CS is achievable.

The invention is not intended to be limited to the preferred versions of the invention described above, but rather is intended to be limited only by the claims set out below. Thus, the invention encompasses all different versions that fall literally or equivalently within the scope of these claims.

What is claimed is:

1. A medical electrode device comprising:
   a. an elongate electrode body having a proximal end and a distal end for insertion into a body of a patient, and
   b. multiple anchoring elements attached laterally to the electrode body proximally before the distal end to fix the electrode body in the patient, the anchoring elements:
      (1) being distributed around a circumference of the electrode body, wherein the anchoring elements are oriented around the circumference in such a way that upon engagement of the anchoring elements in a body part of the patient, a rotation of the electrode body is opposed by a greater resistance in one rotational direction than in an opposite direction, and
      (2) being formed by multiple lamellae distributed around the circumference of the electrode body, wherein each lamella:
         i. has a base extending lengthwise along at least a portion of a length of the electrode body,
         ii. projects radially outwardly from the electrode body to terminate in a tip extending at least substantially parallel to the base, with the length of the base, and also a length of the tip, being greater than a radial distance by which the flange extends outwardly from the electrode body, and
         iii. curves about the circumference of the electrode body.

2. The electrode device of claim 1 wherein the greater resistance upon rotation of the electrode body occurs in a clockwise direction, as viewed from the proximal end of the electrode body.

3. The electrode device of claim 1 wherein the anchoring elements extend curvedly about the circumference of the electrode body.

4. The electrode device of claim 1 wherein three to six lamellae are provided.

5. The electrode device of claim 1 wherein four lamellae are provided.

6. The electrode device of claim 1 wherein the flexural strength of each anchoring element is anisotropic around the circumference of the electrode body.

7. The electrode device of claim 1 wherein the distal end of the electrode body bears an electrode thereon.

8. The electrode device of claim 1 wherein the anchoring elements are resiliently flexible, whereby they may flexibly yield at least partially under pressure, and return to their original shapes once pressure is relieved.

9. The electrode device of claim 1 wherein each lamella defines a continuous surface between the lamella's base and tip.

10. A medical electrode device comprising:
    a. an electrode body having a longitudinal axis extending between a proximal end and a distal insertion end;
    b. an electrically conductive electrode situated on the distal insertion end;
    c. anchoring elements extending outwardly from a circumference of the electrode body, the anchoring elements each:
       (1) being defined by a lamellar flange having a base affixed to the electrode body and an opposing tip spaced from the base, wherein:
          i. an affixed length of the base is substantially greater than a radial distance between the base and the tip, and
          ii. the tip extends at least substantially parallel to the base, the tip also having a length substantially greater than the radial distance between the base and the tip,
       (2) being oriented towards one of a clockwise or counterclockwise direction about the circumference of the electrode body.

11. The medical electrode device of claim 10 wherein the anchoring elements are situated rearwardly of the distal insertion end.

12. The medical electrode device of claim 10 wherein the anchoring elements:
   a. extend rearwardly toward the proximal end, and
   b. have longitudinal axes angled acutely with respect to the longitudinal axis of the electrode body.

13. The electrode device of claim 10 wherein the anchoring elements are resiliently flexible, whereby they may flexibly yield at least partially under pressure, and return to their original shapes once pressure is relieved.

14. The electrode device of claim 10 wherein the anchoring elements have greater flexural rigidity in one of the clockwise or counterclockwise directions than in the other of these directions.

15. The electrode device of claim 10 wherein the anchoring elements extend curvedly about the circumference of the electrode body.

16. The electrode device of claim 10 wherein each lamellar flange defines a continuous surface between the flange's base and tip.

17. A medical electrode device comprising:
   a. an electrode body having a longitudinal axis terminating in an at least substantially cylindrical distal insertion end;
   b. an electrically conductive electrode situated on the distal insertion end;
   c. anchoring elements situated rearwardly of the distal insertion end, the anchoring elements each:
      (1) being defined by a lamellar flange having a base affixed to the electrode body and an opposing tip spaced from the electrode body and extending at least substantially parallel to the base, wherein:
         i. an affixed length of the base is substantially greater than a radial distance by which the flange extends outwardly from the electrode body, and
         ii. the tip has a length at least substantially equal to the affixed length of the base;
      (2) extending:
         i. outwardly from a circumference of the electrode body,
         ii. in one of a clockwise or counterclockwise direction about the circumference of the electrode body, and
         iii. rearwardly toward the proximal end.

18. The electrode device of claim 17 wherein the anchoring elements extend curvedly about the circumference of the electrode body.

19. The electrode device of claim 17 wherein three to six lamellar flanges are provided.

20. The electrode device of claim 17 wherein each lamellar flange defines a continuous surface between the flange's base and tip.

* * * * *